(12) United States Patent
Xu et al.

(10) Patent No.: US 8,498,464 B2
(45) Date of Patent: Jul. 30, 2013

(54) INTRINSIC CO-REGISTRATION FOR MODULAR MULTIMODALITY MEDICAL IMAGING SYSTEMS

(75) Inventors: Ray S. Xu, Algonquin, IL (US); James T. Chapman, Glen Ellyn, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 947 days.

(21) Appl. No.: 12/240,799

(22) Filed: Sep. 29, 2008

(65) Prior Publication Data

US 2009/0087061 A1 Apr. 2, 2009

Related U.S. Application Data

(60) Provisional application No. 60/995,578, filed on Sep. 27, 2007, provisional application No. 60/995,576, filed on Sep. 27, 2007, provisional application No. 60/995,528, filed on Sep. 27, 2007.

(51) Int. Cl.
*G06K 9/32* (2006.01)
*G06K 9/52* (2006.01)
*H05G 1/60* (2006.01)

(52) U.S. Cl.
USPC ............. 382/131; 382/132; 378/20; 378/205; 378/901

(58) Field of Classification Search
USPC   382/129, 131, 132, 181, 293–295; 378/4–20, 378/62, 63, 162–164, 204, 205, 210, 901
See application file for complete search history.

(56) References Cited

U.S. PATENT DOCUMENTS

| | | | | |
|---|---|---|---|---|
| 6,856,666 | B2 * | 2/2005 | Lonn et al. | 378/8 |
| 7,103,233 | B2 * | 9/2006 | Stearns | 382/289 |
| 7,978,895 | B2 * | 7/2011 | Wang et al. | 382/131 |
| 8,077,943 | B2 * | 12/2011 | Williams et al. | 382/128 |
| 2004/0030246 | A1 * | 2/2004 | Townsend et al. | 600/427 |
| 2004/0086199 | A1 * | 5/2004 | Stearns | 382/289 |
| 2007/0116344 | A1 * | 5/2007 | Hsieh et al. | 382/131 |
| 2008/0118132 | A1 * | 5/2008 | Ubelhart et al. | 382/131 |
| 2008/0273654 | A1 * | 11/2008 | Rappoport et al. | 378/18 |
| 2009/0226066 | A1 * | 9/2009 | Williams et al. | 382/131 |
| 2009/0238427 | A1 * | 9/2009 | Hsieh et al. | 382/131 |
| 2009/0253980 | A1 * | 10/2009 | Wollenweber et al. | 600/411 |
| 2010/0290584 | A1 * | 11/2010 | Vesel et al. | 378/9 |
| 2010/0322498 | A1 * | 12/2010 | Wieczorek et al. | 382/131 |

* cited by examiner

*Primary Examiner* — Anastasia Midkiff
(74) *Attorney, Agent, or Firm* — Peter Kendall

(57) ABSTRACT

A method and device are provided for matching a patient coordinate system (PCS) of a nuclear medical imaging scanner with a coordinate system of a CT scanner in a multimodality modular imaging system, based on a predefined relationship between a vertical position of a patient bed during the NM scan; an axial position of the patient bed during the NM scan; an axial distance between a gantry of the NM scanner and a gantry of the CT scanner; and a vertical distance between a center of orbit of the NM scanner and a center of rotation of the CT gantry.

28 Claims, 13 Drawing Sheets

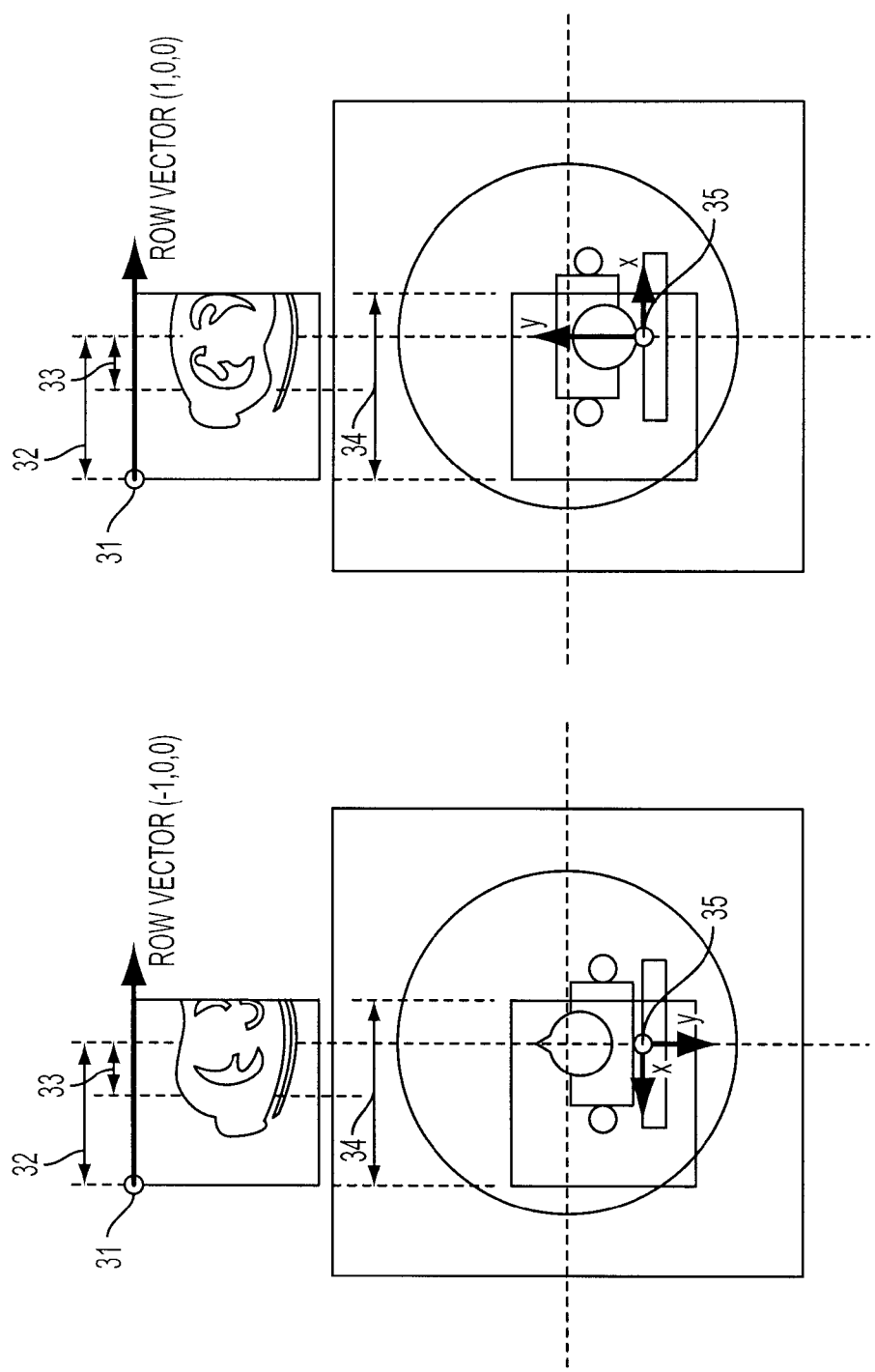

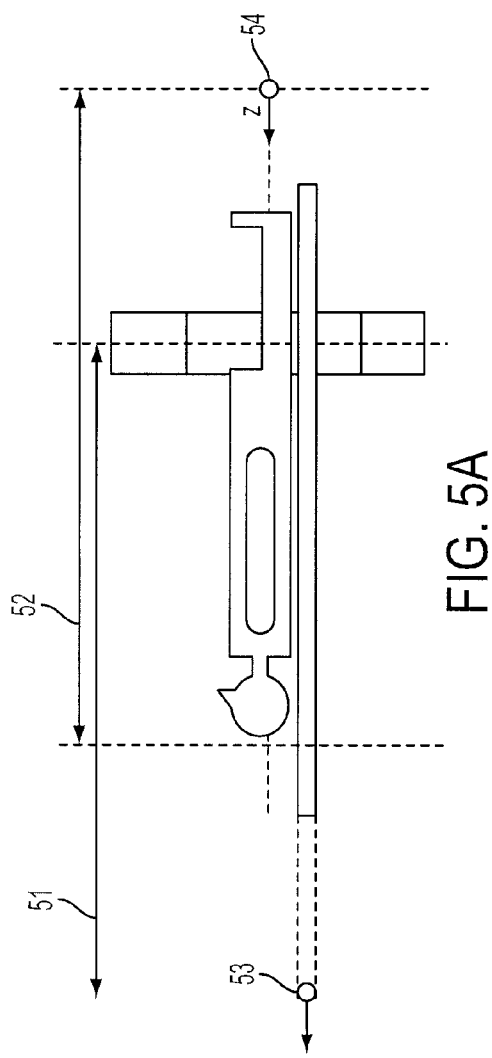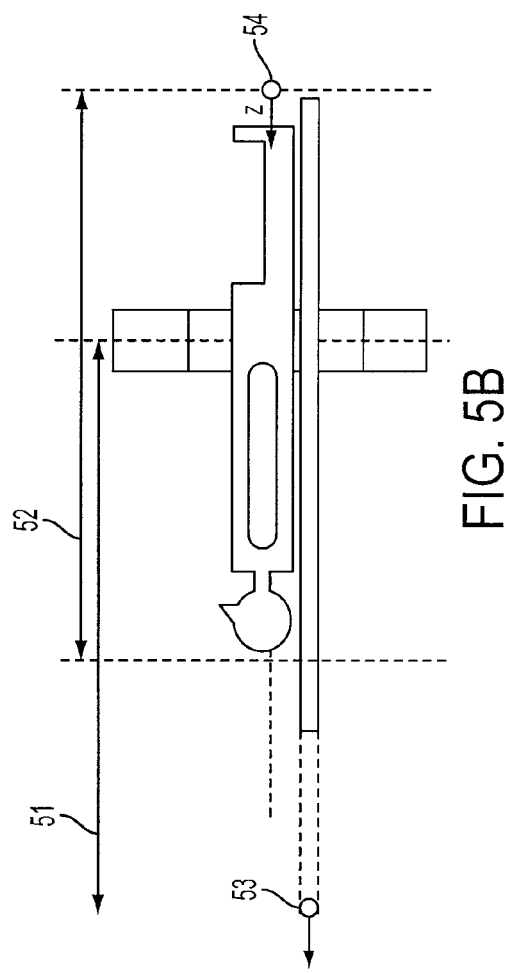
FIG. 5A
FIG. 5B

INTRINSIC CO-REGISTRATION FOR MODULAR MULTIMODALITY MEDICAL IMAGING SYSTEMS

CROSS-REFERENCES TO RELATED APPLICATIONS

This application claims benefit under 35 U.S.C. §119(e) to:
U.S. Provisional Patent Application Ser. No. 60/995,528 filed on Sep. 27, 2007;
U.S. Provisional Patent Application Ser. No. 60/995,576 filed on Sep. 27, 2007; and
U.S. Provisional Patent Application Ser. No. 60/995,578 filed on Sep. 27, 2007,
which are hereby incorporated by reference in their entireties.

BACKGROUND OF THE INVENTION

The present invention describes how intrinsic co-registration of Nuclear Medicine (NM) and Computed Tomography (CT) transverse images is achieved for Modular Multimodality Nuclear Medical Imaging Systems.

For loosely-coupled modular multi-modality imaging systems, such as cardiac SPECT-CT systems that share the same patient table, but do not have any common installation platform, it is necessary to calibrate the separate imaging modules so that their images may be fused or combined into a composite image that is clinically useful.

DESCRIPTION OF THE RELATED ART

In modular multi-modality medical imaging systems, wherein modules may be added and combined in a flexible manner, the modules are loosely integrated in that they do not share any common installation platform. In order to make use of multi-modality imaging, the modules must be co-registered with respect to their FOVs so that the images produced by the separate modules can be fused or combined into a composite image for clinical analysis.

BRIEF SUMMARY OF THE INVENTION

In accordance with the invention, a method and device for co-registering a nuclear medical (NM) reconstructed image obtained from an NM scan by an NM scanner having an NM gantry, and a computed tomography (CT) reconstructed image obtained from a CT scan by a CT scanner having a CT gantry in a multimodality imaging system are provided, wherein matching of a first patient coordinate system of the NM scanner to a second coordinate system of the CT scanner, is based on a predefined relationship between:
  a vertical position of a patient bed during the NM scan;
  an axial position of the patient bed during the NM scan;
  an axial distance between a gantry of the NM scanner and a gantry of the CT scanner; and
  a vertical distance between a center of orbit of the NM scanner and a center of rotation of the CT gantry.

BRIEF DESCRIPTION OF THE DRAWINGS

These and other features, aspects, and advantages of the present invention will become better understood with reference to the following description and appended claims, and accompanying drawings where:

FIGS. 3(a), 3(b), 3(c), and 3(d) show determinations of the X coordinate for CT images;

FIGS. 5(a) and 5(b) show how CT assigns Z positions in the Feet First (FF) patient orientations;

DETAILED DESCRIPTION OF THE INVENTION

In the following detailed description and in the claims which follow, reference will be made to a number of terms which shall be defined to have the following meanings:

Computed (or Computerized) Tomography (CT): An imaging technique that uses X-ray views of an object from many directions to synthesize a transaxial or cross sectional image.

Field Of View (FOV): size of an area being imaged.

Digital Imaging and Communications in Medicine (DICOM): refers to a global information-technology standard developed in 1993 to ensure the interoperability of systems used to produce, store, display, process, send, retrieve, query, or print medical images and derived structured documents as well as to manage related workflow.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

The present invention reliably and efficiently achieves intrinsic co-registration of NM and CT transverse images for Modular Multimodality Nuclear Medical Imagining Systems.

In particular, the present invention reliably and efficiently matches a patient coordinate system (PCS) of NM reconstructed images to a patient coordinate system of CT reconstructed images.

Preferably, the present invention addresses translation registration (X, Y, and Z) in PCS only, it being assumed that no rotational misalignment exists between the CT and NM systems. Such misalignments are corrected by a Field of View (FOV) calibration procedure, as described in the above-referenced provisional application Ser. No. 60/995,576.

Figure 1:
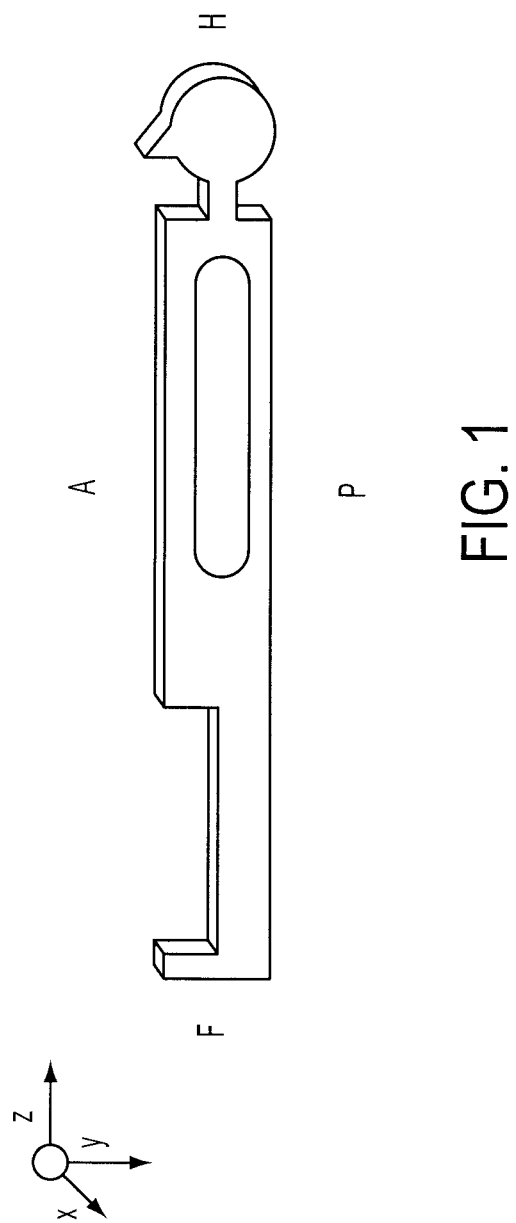
FIG. 1 shows a Digital Imaging and Communications in Medicine (DICOM) patient co-ordinate system (PCS)

FIG. 1 shows the axes of a DICOM Patient Coordinate System (PCS). According to FIG. 1, "H" stands for "head." "F" stands for "feet." "A" stands for "anterior." "P" stands for "posterior." DICOM defines a coordinate system based on which positions and orientations are assigned to patient images. The DICOM standard defines only the directions of the axes of the PCS with respect to the patient. An origin is not specified by the standard. However, for NM reconstruction and CT transverse image sets to be spatially registered, they must use a common origin for the PCS.

Figure 2:
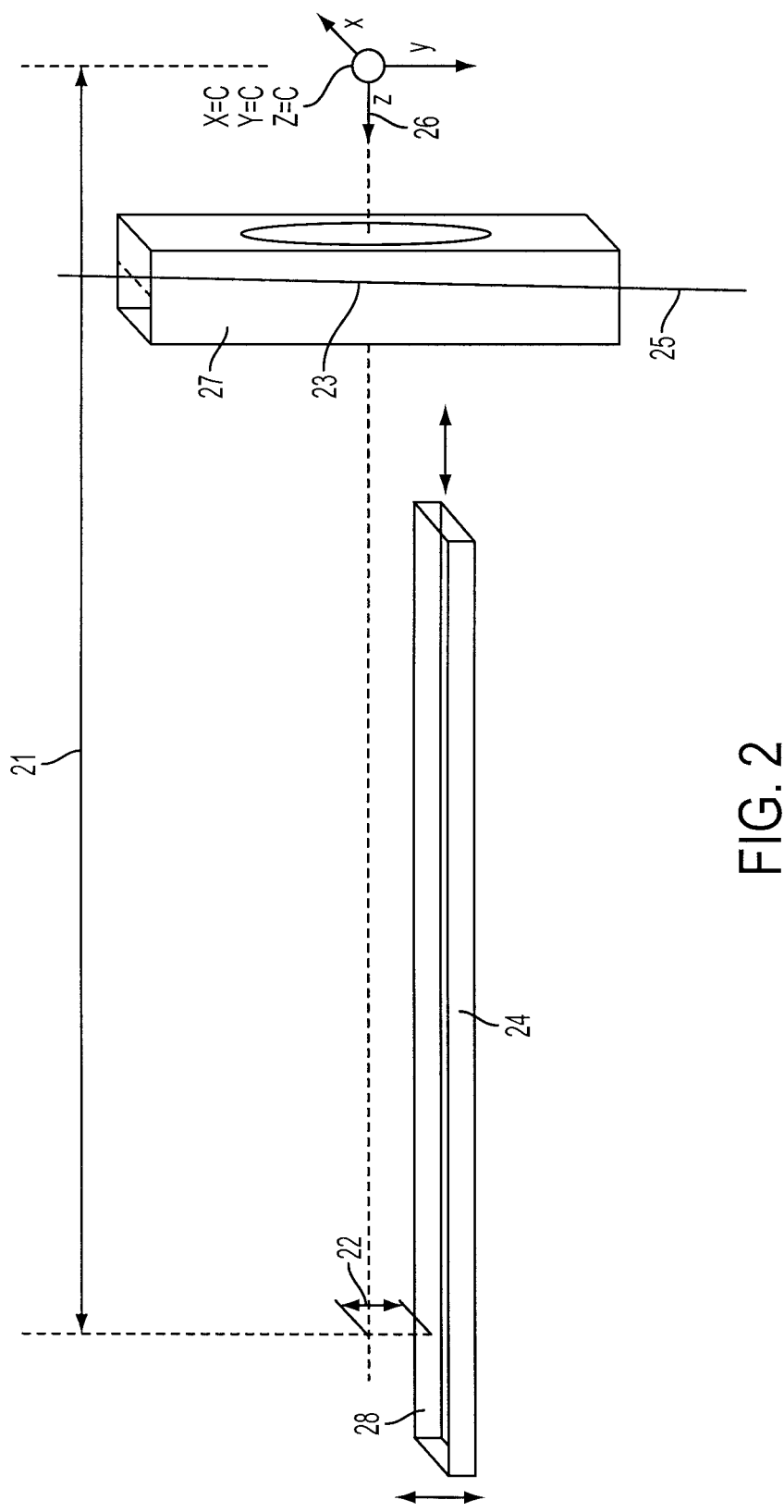
FIG. 2 shows a Computed Tomography (CT) Device coordinate system (DCS)

FIG. 2 shows a CT Device Coordinate System (DCS). The SENSATION64™ system, a 64-slice CT system available from Siemens Corporation, has a fixed coordinate system based on which positions are displayed on the UI and gantry panel. The device coordinate system is "fixed" in that the origin and axis directions are fixed. This fixed coordinate system is independent of how the patient is oriented on the scanner. In other words, the coordinate system is "fixed" to the CT gantry.

Still referring to FIG. 2, the X and Y positions of the origin are fixed at the center of rotation (COR) of the CT gantry, while the Z position of the origin can be set by the user. For example, the user can set the Z position by pressing the "zero" button when the patient bed is at any particular position with respect to the gantry. As shown in FIG. 2, the orientation of Z is fixed. According to preferred embodiments of the present invention, the Z origin is not changed between NM and CT scans. In other words, it is preferable to assume that the "zero" button is not used to change the Z origin between NM and CT scans.

Still referring to FIG. 2, a patient bed (24) is provided relative to a CT scanner (27). The CT scanner (27) has a center of rotation (23) and a field of view (FOV), having a centerline (25). The position of bed (24) is preferably reported by the CT system regardless of which type of scan is being performed. The Z and Y positions of the bed in this DCS are designated as $Z_{bed}$ (21) and $Y_{bed}$ (22) during a CT scan, and $Z_{NMbed}$ and $Y_{NMbed}$ during an NM scan. $Y_{bed}$ (22) measures the bed position between the DCS origin ($X_0$, $Y_0$, $Z_0$) (26) and the top surface (28) of the bed. The bed (24) moves in the DCS and the patient lies on the bed. Therefore, the PCS moves in the CT DCS. The PCS moves in conjunction with the motion of the bed. For example, as the bed moves up and down, back and forth, the PCS moves up and down, back and forth. In other words, the PCS is fixed to the patient bed.

Figure 3C:
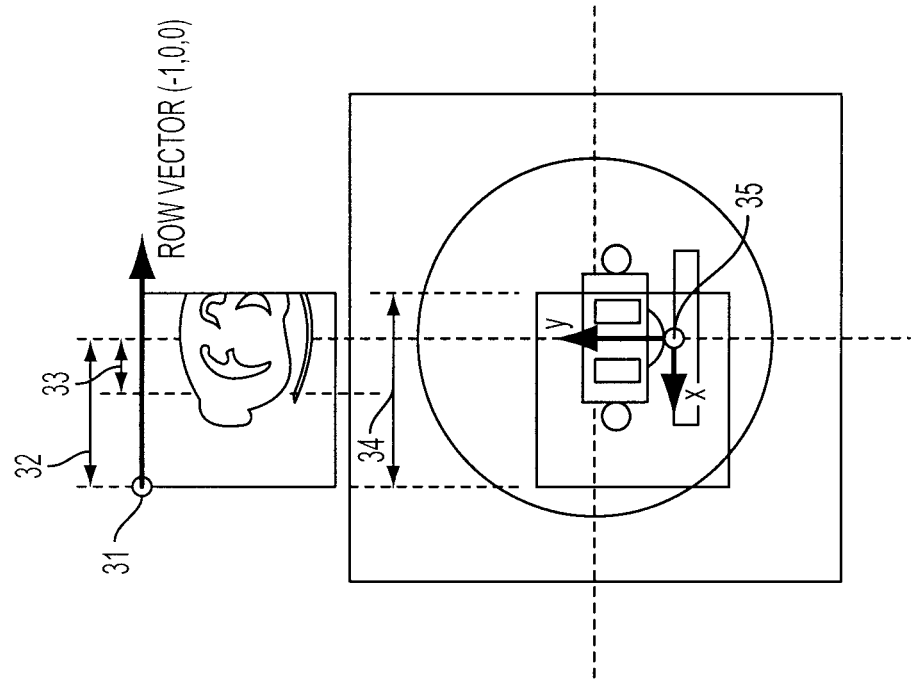
Figure 3D:
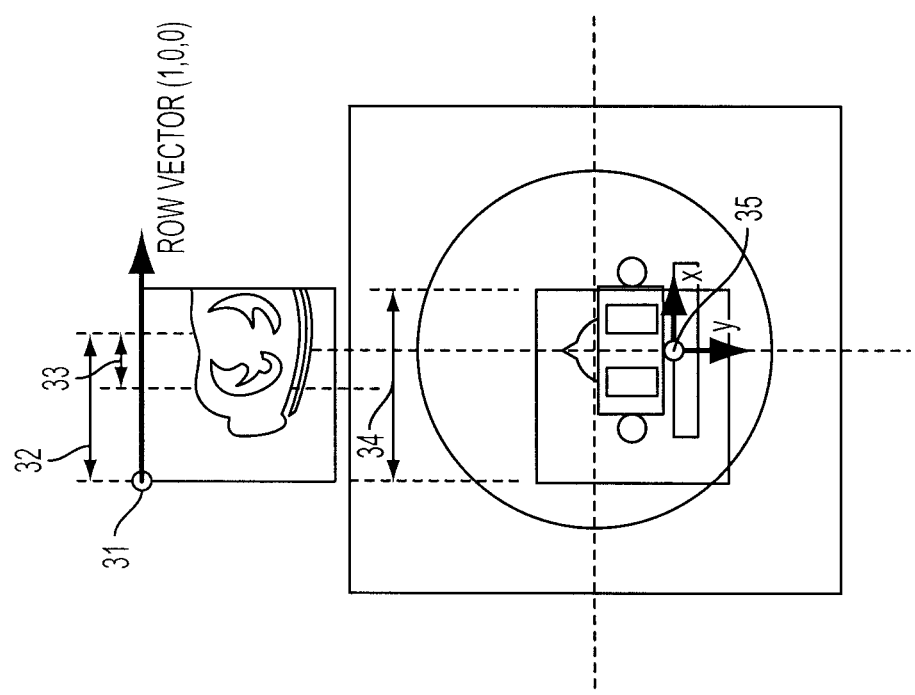

FIGS. 3(a), 3(b), 3(c) and 3(d) show determinations of the X coordinate for CT images. In particular, FIG. 3(a) shows a patient oriented face-up with the patient's head facing the plane of the figure; FIG. 3(b) shows a patient oriented face-down with the patient's head facing the plane of the figure; FIG. 3(c) shows a patient oriented face-up with the patient's feet facing the plane of the figure; and FIG. 3(d) shows a patient oriented face-down with the patient's feet facing the plane of the figure. The CT scanner assigns X-axis coordinates to transverse slices.

The origins of both CT DCS and DICOM PCS, which respectively lie at the center of the CT gantry and the center of the patient bed, overlap in space in the Y (i.e., up-down) direction, as shown in FIGS. 3(a)-3(d). The position of an image in PCS is preferably determined by that of its top-left pixel (31), which can also be referred to as the pixel in the first row and first column of an image. The so-called row vector [$rv_x$, $rv_y$, $rv_z$] is properly set into the CT image to specify how the image is oriented relative to the PCS.

CT allows image reconstructions on any region within the imaged area. Therefore, the image center and the transverse extents of the reconstructed image are preferably specified. The image center is preferably specified as a distance, $X_{center}$ (33), of the center of the PCS from the center of the CT DCS, and the transverse extents of the image are preferably specified as the size of the square (i.e., the FOV 34) centered at the image center point (35). Note that $X_{center}$ (33) could be either positive or negative, depending upon the direction along the x-axis of the PCS that the image center was shifted. For instance, with the PCS oriented as shown in FIG. 1, $X_{center}$ (33) is shifted negatively in FIGS. 3(a) and 3(d), and positively in FIGS. 3(b) and 3(c).

As can be seen from FIGS. 3(a), 3(b), 3(c), and 3(d), $X_{img}$ (32) is preferably given by Equation 1:

$$X_{img} = X_{center} - (rv_x)(1/2)(FOV_{CT})$$ 1, where (½)(FOVC$_{CT}$) is preferably given by Equation 2:

$$(1/2)(FOV_{CT}) = (MatrixSize_{CT} - 1)(PixelSize_{CT}/2)$$ 2.

Note that (MatrixSize−1) is preferably used instead of MatrixSize because DICOM specifies that the center of a slice or pixel is the reference point of its spatial position in PCS. $X_{img}$ (32) is preferably stored as Value_1 in the DICOM attribute (0020, 0032) of the CT image.

For NM projections, the x coordinate does not have any meaning (because the NM projection is taken in the y-z plane). Thus, it is preferable to set Value_1 in the DICOM attribute (0020, 0032) of the raw NM image to 0.

NM post-processing assigns x coordinates to transverse slices. If the transverse images shown in FIGS. 3(a), 3(b), 3(c), and 3(d) are reconstructed by NM post-processing S/W, the distance between the center of the NM image and the center of the PCS in X direction becomes $X_{NMcenter}$ instead of $X_{center}$.

The NM tomographic views are back-projected to the center of rotation (COR) of the NM gantry, and it is assumed that the X-axis of the modular multimodality nuclear medical imaging system orbit is aligned with the center of rotation (COR) of the CT by mechanical means. Therefore, $X_{NMcenter} = 0$. In addition, the NM post processing reconstructs the projections in such a way that the row vector of the reconstructed image is always [1, 0, 0]. Thus, Equation 1, combined with Equation 2 becomes:

$$X_{NMImg} = (MatrixSize_{NM} - 1)(PixelSize_{NM}/2)$$ 3.

$X_{NMImg}$ is preferably stored as Value_1 in the DICOM attribute (0020, 0032) of the reconstructed NM image.

Figure 4A:
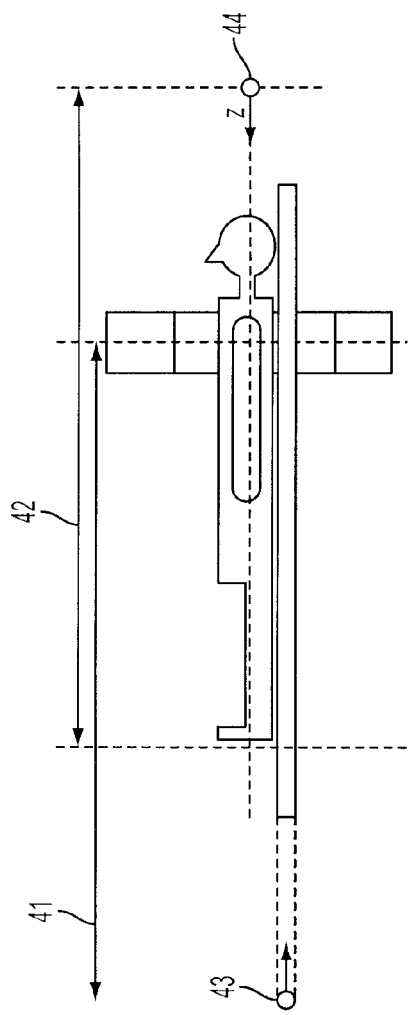
FIGS. 4(a), and 4(b) show how CT assigns Z positions in the Head First (HF) patient orientations.
Figure 4B:
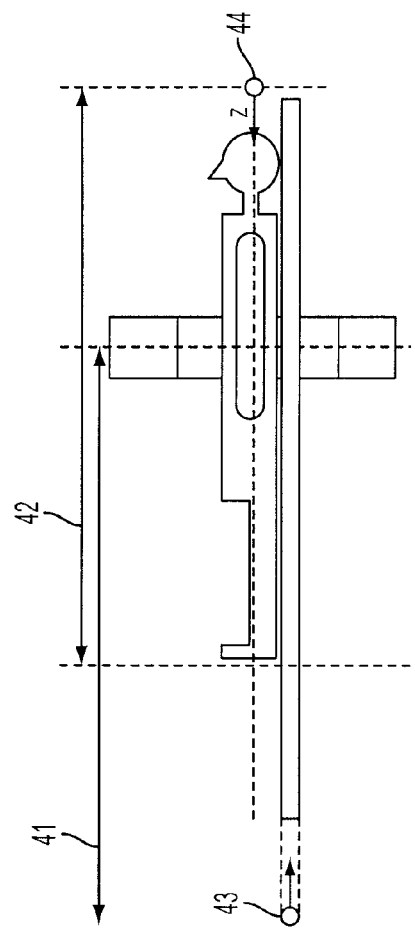

The present invention provides co-registration along the z-axis for modular multimodality NM imaging systems. CT assigns z coordinates to transverse slices. The z-position assigned to an image depends on the orientation of the patient on the bed. FIGS. 4(a) and 4(b) show how a Z bed position is preferably transformed into a Z-position of a CT image when a patient is scanned head first (HF).

In the orientation as shown in FIGS. 4(a) and 4(b), the bed moves along the z-axis from the patient origin (43) into the gantry toward the device origin (44). As the bed moves into the gantry, $Z_{bed}$ (42) decreases, and the z-position of a transverse slice to be imaged with respect to the patient decreases by the same proportion, i.e., the slice moves towards the patient's feet. DICOM does not specify the location of the origin of PCS. In other words, the patient origin (43) is not at a specified point along the z-axis. Thus, the CT system sets the z-position of PCS origin (43) to ensure that $Z_{img}$ (41) is the same as $Z_{bed}$ (42), i.e., such that:

$$Z_{img} = Z_{bed}$$ 4.

FIGS. 5(a) and 5(b) show how the Z bed position is preferably transformed into Z image position when the patient is scanned feet-first (FF). In this orientation, as the bed moves into the gantry from patient origin (53) toward the device origin (54), $Z_{bed}$ (52) decreases. As $Z_{bed}$ (52) decreases, the z-position of a transverse slice to be imaged with respect to the patient increases (slice moves towards patient's head). Again, the CT system preferably assigns the location of the PCS origin (53) to ensure that $Z_{img}$ (51) is the additive inverse of $Z_{bed}$ (52), i.e., such that:

$$Z_{img} = -Z_{bed}$$ 5.

Note that the origin (53) of $Z_{bed}$ (52) is preferably a fixed position relative to the patient bed, and the origin (54) of $Z_{img}$ (51) is a fixed position relative to the CT gantry. The two origins can only physically overlap in space if the device origin is "zeroed" at the center of the gantry and when $Z_{img}=Z_{bed}=0$. $Z_{img}$ is preferably stored as Value_3 in the DICOM attribute (0020, 0032) of the CT image.

The NM projection image is oriented such that the top of the image is close to the patient's head and the bottom of the image is close to the patient's feet. In DICOM terminology, the column vector [$cv_x$, $cv_y$, $cv_z$] of any projection image is [0, 0, -1].

The z-position of the projection image in PCS is preferably defined as that of the top row, $Z_{NMImg}$, and the z-positions of other rows can be derived based on the column vector and the distances to the top row. For example, $Z_{NMCenter}$, the z-position of the center row of the projection image, is preferably derived according to Equation 6.

$$Z_{NMCenter}=Z_{NMImg}+(CV_z)(\tfrac{1}{2})(FOV_{NM})=Z_{NMImg}-(\tfrac{1}{2})(FOV_{NM}) \qquad 6,$$

where:

$$(\tfrac{1}{2})(FOV_{NM})=(MatrixSize_{NM}-1)(PixelSize_{NM}/2) \qquad 7.$$

With respect to the same anatomical transverse slice, the image positions of both CT and NM images in PCS must be the same, that is, $$Z_{NMCenter}=Z_{img} \qquad 8.$$

Figure 6:
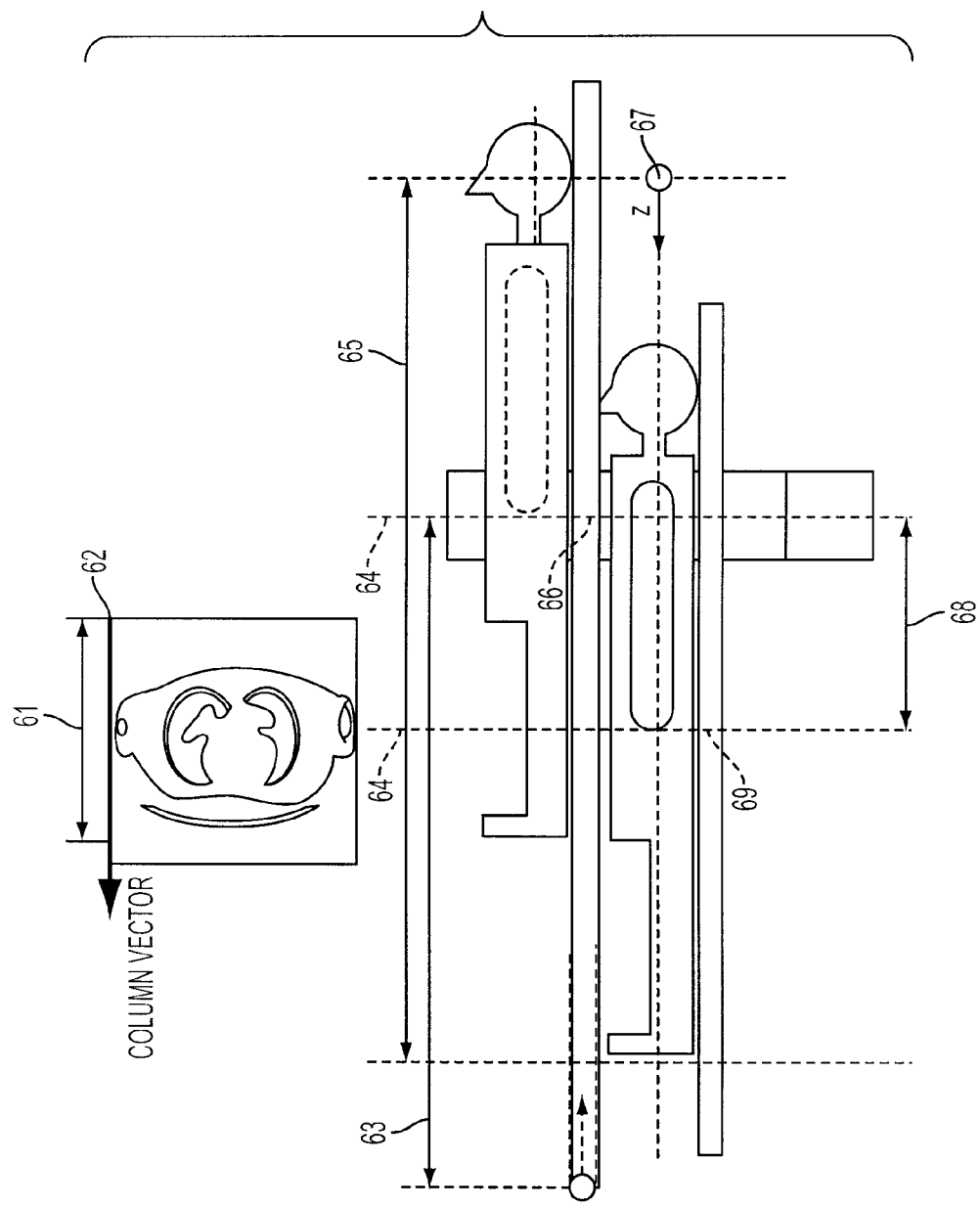
FIG. 6 shows Z position assignment in HF patient orientations in a modular multimodality nuclear medical imagining system.
Figure 7:
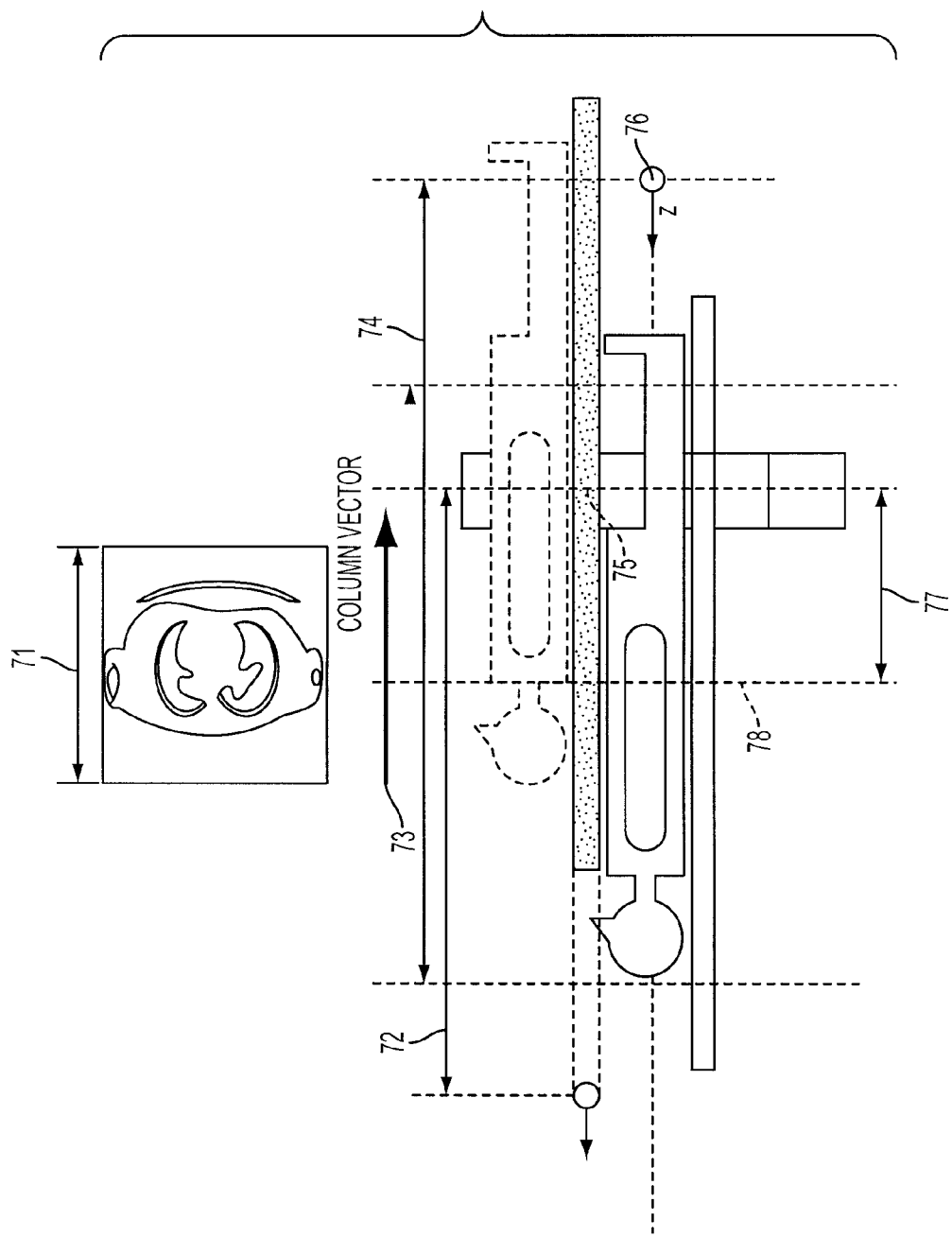
FIG. 7 shows Z position assignment in the FF patient orientations in a modular multimodality nuclear medical imagining system.

The patients shown in FIG. 6 and in FIG. 7 are being imaged by the NM gantry (69, 78) with the bed position of $Z_{NMBed}$ (65, 74). The bed travels an extra distance of $Z_{gantry}$ (68, 77) toward the CT gantry (66, 75) and toward the device origin (66, 76). The same center slice (64) is preferably imaged by CT, as shown by the shaded picture of the patient and bed in the diagram. The image has a FOV (61, 71), and a first row/column (62, 73). Therefore, $$Z_{bed}=Z_{NMBed}-Z_{gantry} \qquad 9.$$

In FIG. 6, the patient is scanned head-first (HF). Thus, combining Equation 4, Equation 6, Equation 8, and Equation 9 yields:

$$Z_{NMImg}=Z_{NMbed}-Z_{gantry}+(\tfrac{1}{2})(FOV_{NM}) \qquad 10.$$

In FIG. 7, the patient is imaged feet-first (FF). Thus, combining Equation 5, Equation 6, Equation 8, and Equation 9 yields:

$$Z_{NMImg}=-Z_{NMbed}+Z_{gantry}+(\tfrac{1}{2})(FOV_{NM}) \qquad 11.$$

Note that $Z_{gantry}$ would be negative if the Modular Multimodality NM imaging system gantry lies behind the CT gantry. The $Z_{NMImg}$ (63, 72) is preferably stored as Value_3 in the DICOM attribute (0020, 0032) of the projection image for all NM views.

According to another aspect of the present invention, NM post-processing also assigns Z coordinates to transverse slices. The NM post-processing S/W, according to the present invention, is able to handle the raw projection images with different column vectors, [0, 0, 1] or [0, 0, -1]. Preferably, the NM post-processing S/W sets the DICOM spacing between slices (0018, 0088) to be positive. If it is assumed that the projection column vector is [0, 0, -1] and the full reconstruction range, then the $Z_{NMImg}$ (63, 72) extracted from the raw projection image is preferably transferred to the reconstructed image as Value_3 in the DICOM attribute (0020, 0032).

The present invention also provides co-registration along the Y-axis. In modular multimodality NM imaging systems the patient moves with the bed. Preferably, for either the NM or the CT transverse image, the Y-origin of the PCS is always the upper surface of the bed along its center axis.

CT assigns Y coordinates to transverse slices. CT allows reconstructions on any region in the imaged area. Therefore, the image center and the transverse extents of the reconstructed image are preferably specified. The image center is preferably specified as the distance ($Y_{Center}$) from the COR of CT gantry, and the transverse extents are preferably specified as the size of the square centered at the image center point (FOV). Note that $Y_{Center}$ would be negative if it is above the CT COR.

Figure 8A:
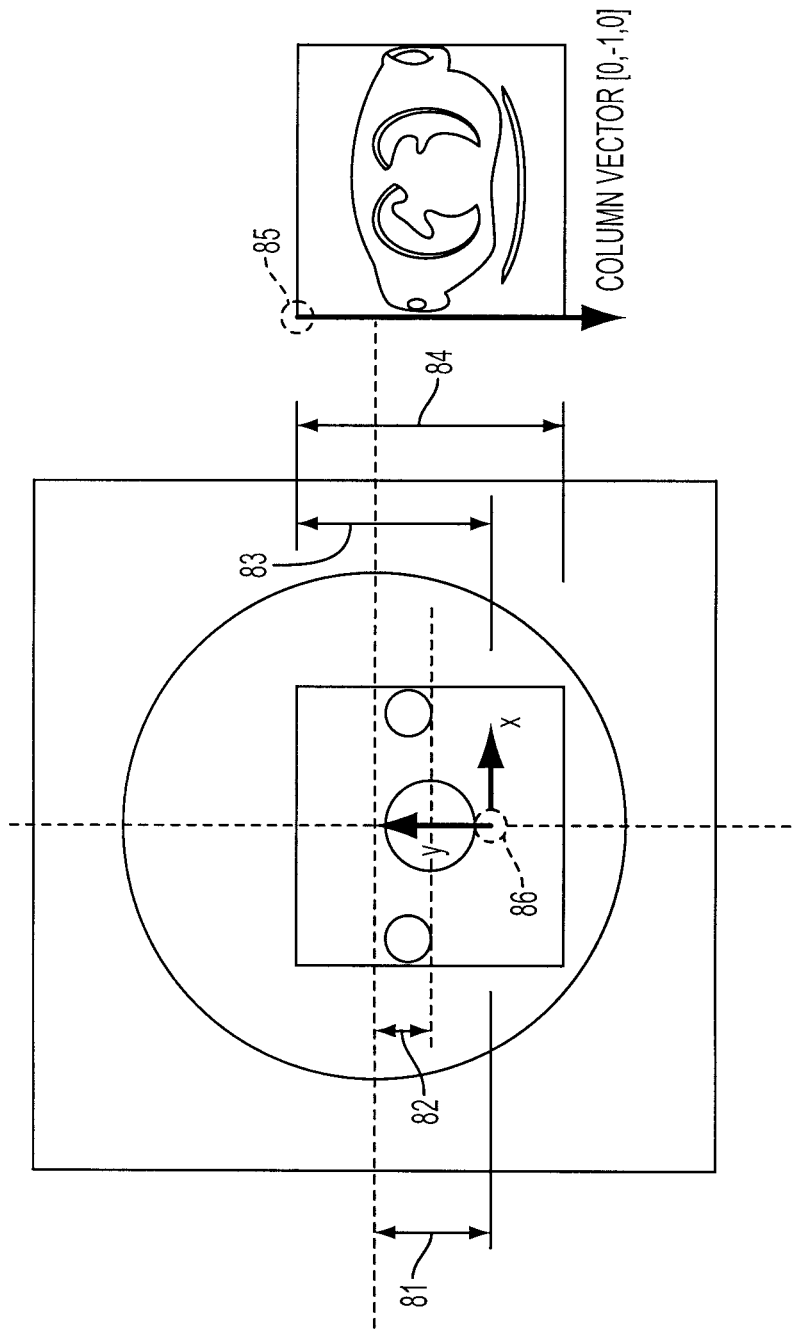
FIGS. 8(a) and 8(b) show Y position assignment in CT transverse images according to one method.
Figure 8B:
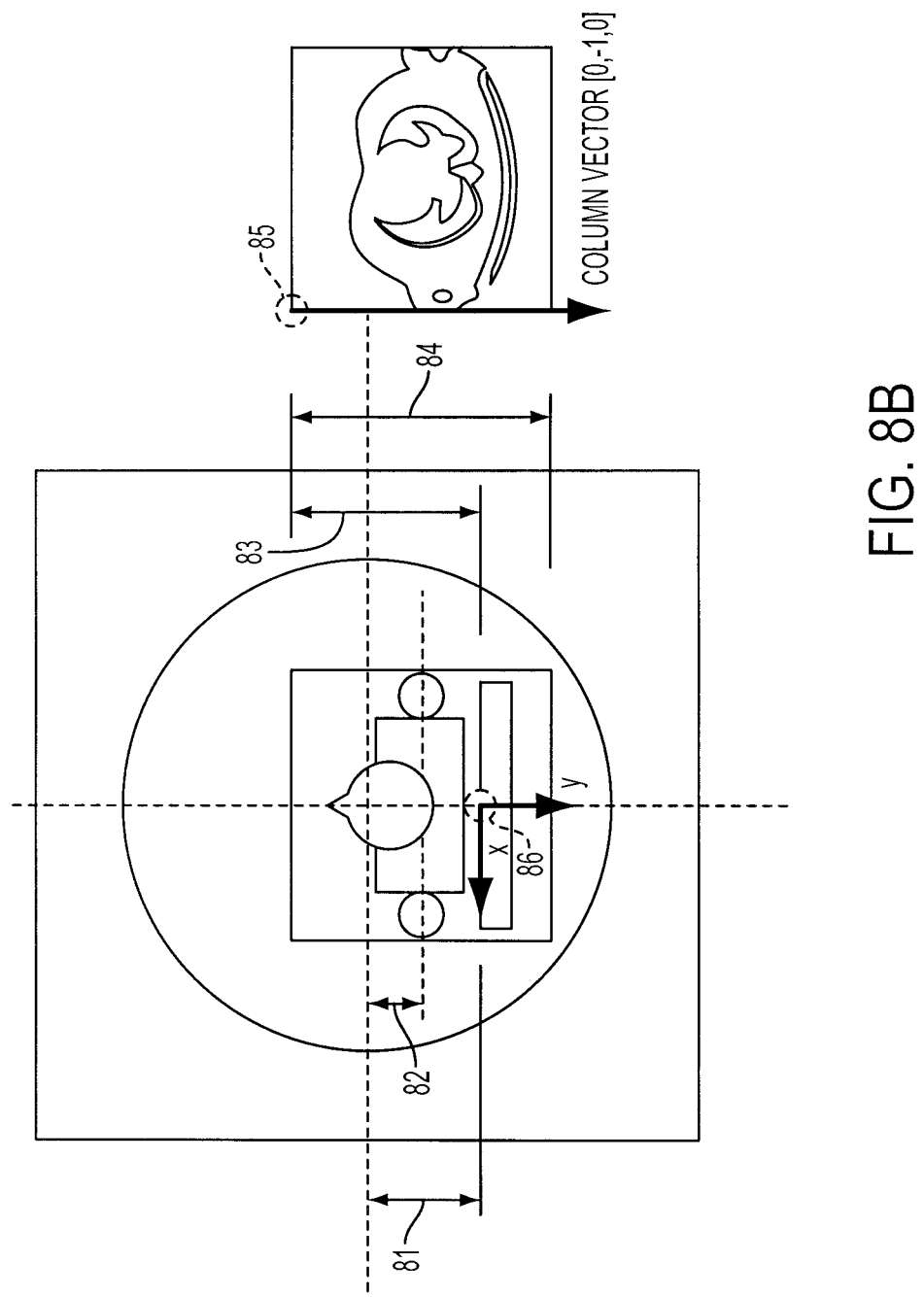

FIGS. 8(a) and 8(b) show one method of Y-position assignment in CT transverse images. The column vector of a CT transverse image, when viewed in the CT DCS, points to the same direction of the Y-axis of the PCS. $Y_{bed}$ (81) is the distance from the bed to the COR of the CT gantry. $Y_{Center}$ (82) is the distance from the COR of the CT gantry to the center of the image. $Y_{Img}$ (83) is the distance from the first row/column (85) of the image to the origin of the PCS (86). FOV (84) is the size of the square centered at the image center point.

In this way of viewing a transverse image, the column vector [$cv_x$, $cv_y$, $cv_z$] of the image is [0, -1, 0] when the patient is preferably scanned in a prone position (FIG. 8(a)), and [0, 1, 0] in a supine position (FIG. 8(b)). Thus, we have:

$$Y_{Img}=(-cv_y)(Y_{Bed}-Y_{center}+(\tfrac{1}{2})(FOV_{CT})) \qquad 12.$$

Figure 9A:
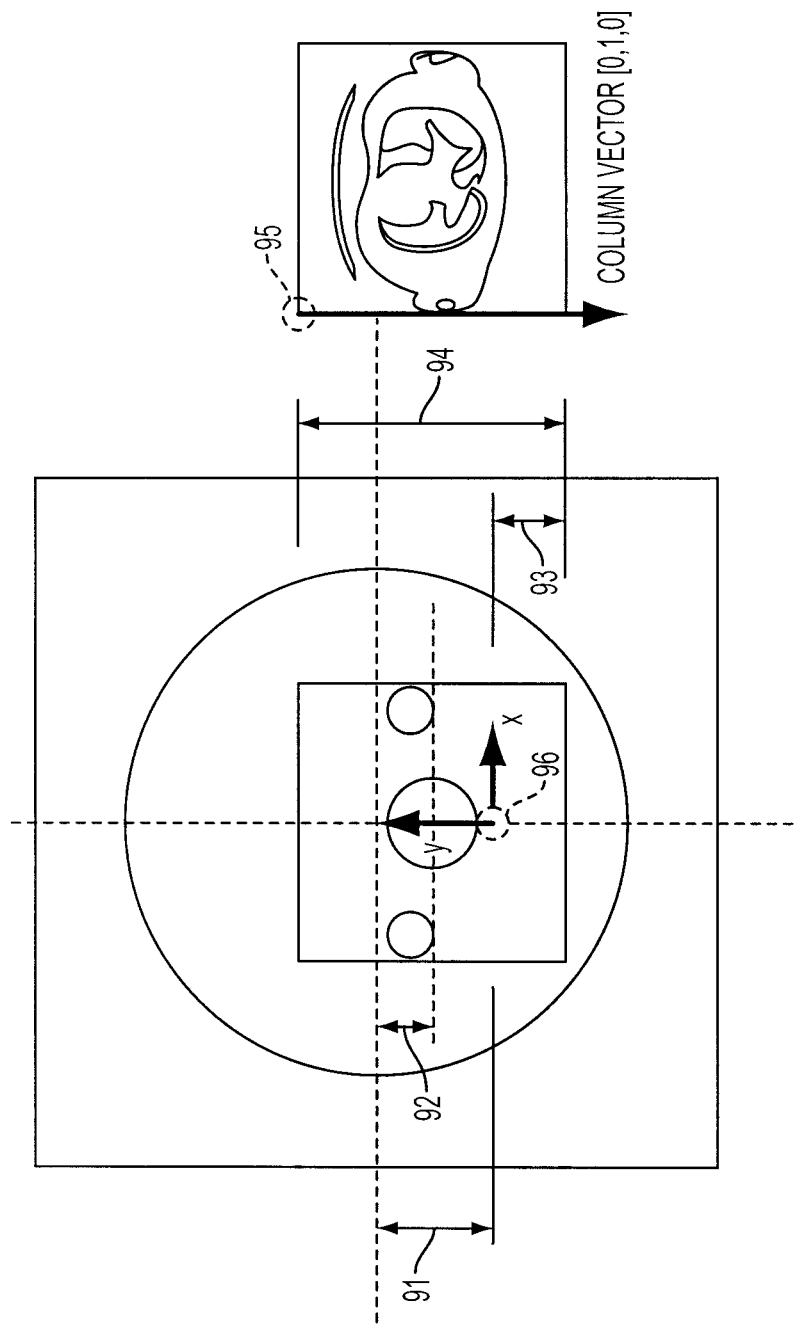
FIGS. 9(a) and 9(b) show Y position assignment in CT transverse images according to another method.
Figure 9B:
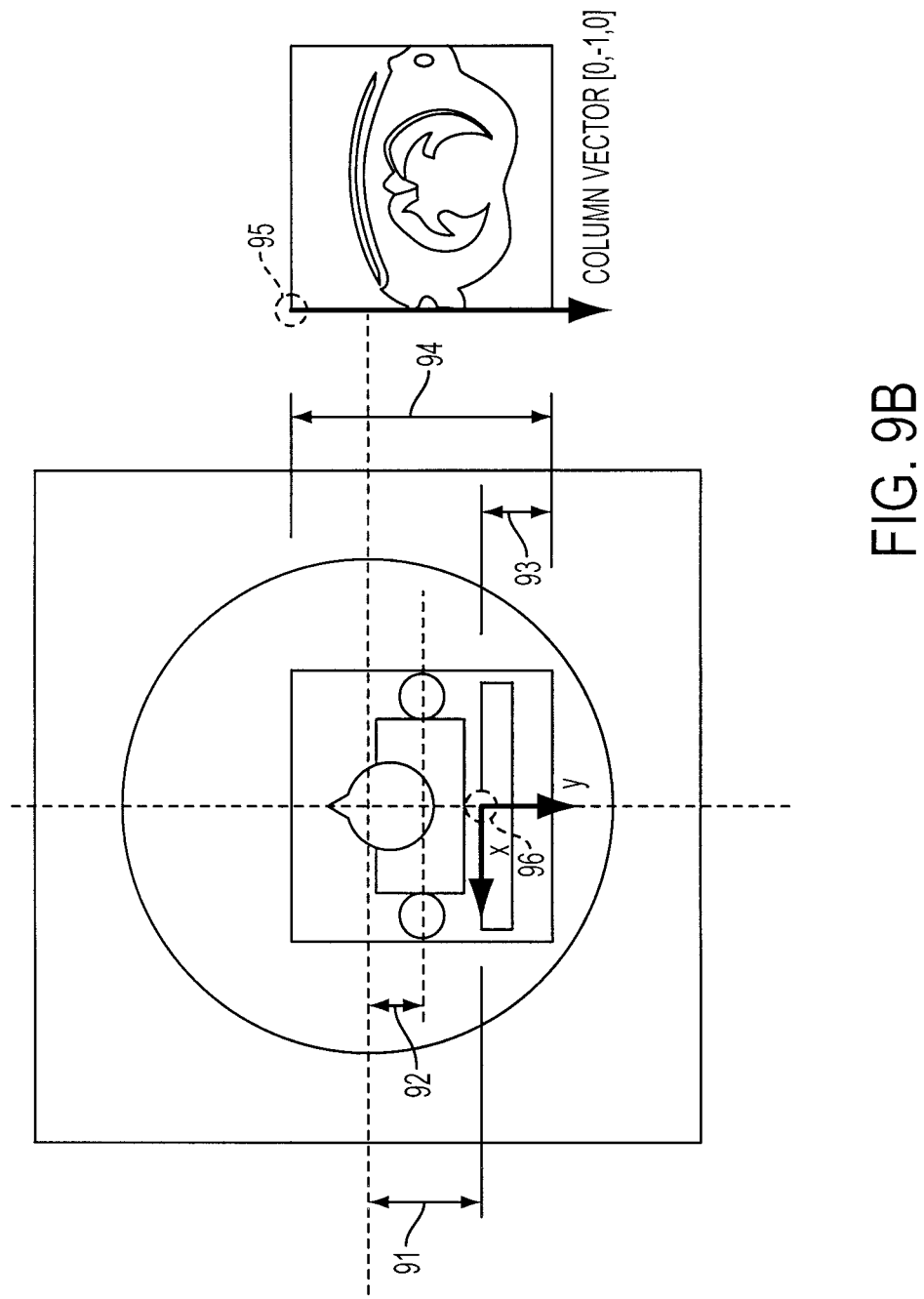

FIGS. 9(a) and 9(b) show a second method of Y-position assignment in CT transverse images. In FIGS. 9(a) and 9(b), the column vector of a CT transverse image, when viewed in the CT DCS, points to the opposite direction of the Y-axis of the PCS. $Y_{bed}$ (91) is the distance from the bed to the COR of the CT gantry. $Y_{Center}$ (92) is the distance from the COR of CT gantry to the center of the image. $Y_{Img}$ (93) is the distance from the first row/column (95) of the image to the origin of the PCS (96). FOV (94) is the size of the square centered at the image center point. Note that in FIG. 9(a) $Y_{Img}$ (93) is negative.

In this way of viewing a transverse image, though untypical, the column vector [$cv_x$, $cv_y$, $cv_x$] of the image is [0, 1, 0] when the patient is scanned in a prone position (FIG. 9(a)), and [0, -1, 0] in a supine position (FIG. 9(b)). Thus, we have:

$$Y_{Img}=(-cv_y)(Y_{Bed}-Y_{center}+(\tfrac{1}{2})(FOV_{CT})) \qquad 13.$$

The method of Y-position assignment in CT transverse images illustrated in FIGS. 8(a) and 8(b) and the method of Y-position assignment in CT transverse images illustrated in FIGS. 9(a) and 9(b) are equally valid, depending on the viewing preference set by the user or the manufacturer. In both methods, $Y_{Img}$ is preferably stored as Value_2 in the DICOM attribute (0020, 0032) of the CT image.

The present invention further assigns Y coordinates to projection images in modular multimodality NM imaging systems. For NM projection images, the y coordinate does not have any meaning. Thus, it is preferable to set the Value_2 in the DICOM attribute (0020, 0032) of the raw NM image to 0.

NM Post-processing assigns Y coordinates to transverse slices. If the transverse images as shown in FIGS. 8 and 9 are reconstructed by NM post-processing S/W. The distance in the Y direction between the center of the NM image and the COR of CT gantry becomes $Y_{NMCenter}$ instead of $Y_{Center}$. Preferably, NM tomographic views are back-projected to the COR of the NM gantry. It is also preferable that the NM post-processing image is always [0, 1, 0] regardless of whether the patient is in prone or supine position. Thus, Equation 12 and Equation 13 preferably become Equation 14 for supine scans and Equation 15 for prone scans.

For Supine Scans:

$$Y_{NMImg} = Y_{NMCenter} - Y_{NMBed} - (½)(FOV_{NM}) \quad (14)$$

For Prone Scans:

$$Y_{NMImg} = Y_{NMBed} - Y_{NMCenter} - (½)(FOV_{NM}) \quad (15)$$

$Y_{NMImg}$ is preferably stored as Value_2 in the DICOM attribute (0020, 0032) of the reconstructed NM image.

The following H/W parameters are needed: $Z_{NMBed}$, $Y_{NMBed}$, $Z_{Gantry}$, and $Y_{NMCenter}$. $Z_{NMBed}$ and $Y_{NMBed}$ are the bed positions during the NM scan as shown in FIG. 6, and FIG. 8. $Z_{NMBed}$ and $Y_{NMBed}$ are also saved in NM DICOM images as Table Traverse and Table Height. $Z_{Gantry}$ is the axial distance between two gantries, for example an NM gantry and a CT gantry. See, FIG. 6, for example. $Y_{NMCenter}$ is the vertical distance between the center of NM orbit and the CT gantry, as shown for example in FIG. 10.

Figure 10:
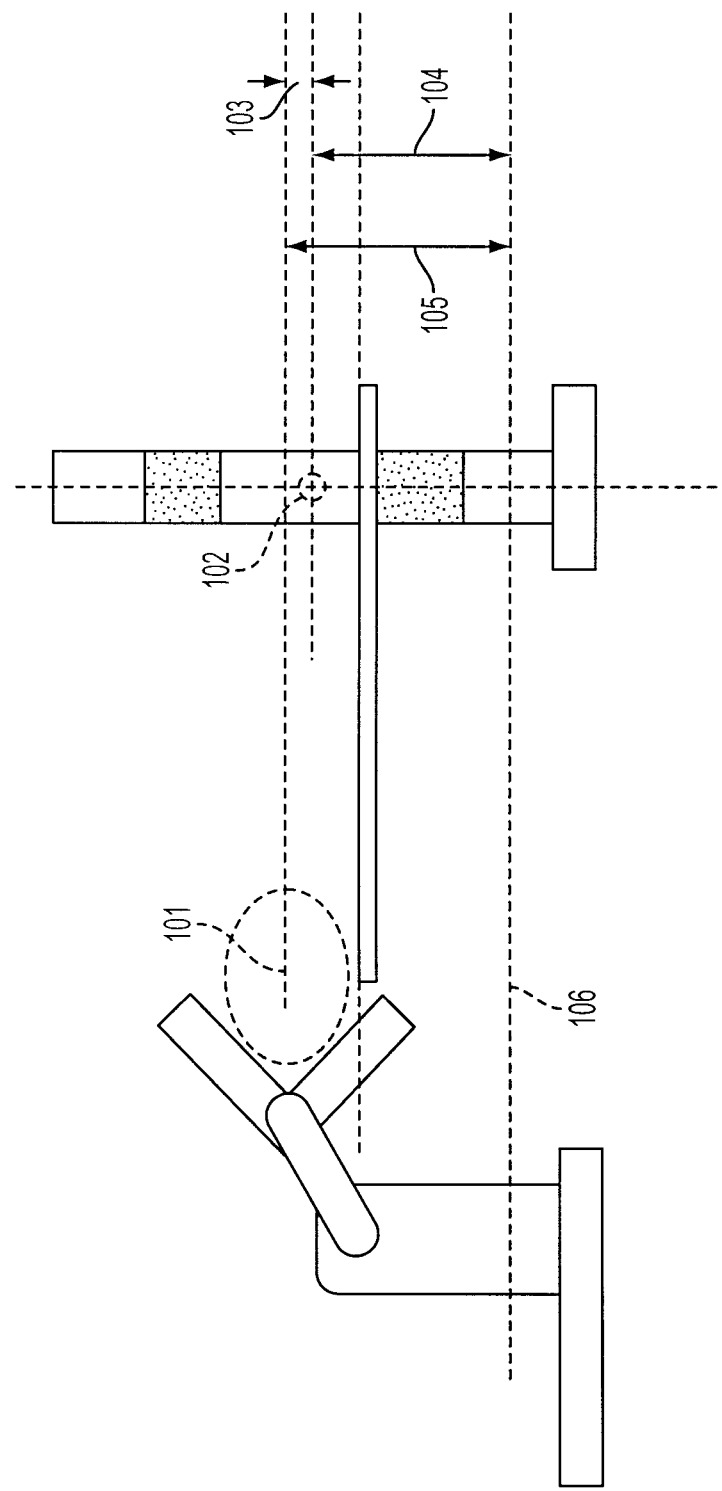
FIG. 10 shows how $Y_{NMCenter}$ may be calculated.

FIG. 10 shows how $Y_{NMCenter}$ (103) is preferably derived for a modular multimodality NM imaging system. Note that all measurements in FIG. 10 are in CT DCS, i.e., the positive Y direction points downward from the centers of rotation (101) of the CT gantry or the NM orbit.

$$Y_{NMCenter} = Y_{CT} - Y_{NM} \quad (16)$$

In Equation 16, $Y_{NM}$ (105) is the height from a fixed common reference line (106) to the center of rotation (COR) of the NM orbit in CT DCS. $Y_{CT}$ (104) is the height from the fixed common reference line to the CT COR (102) in CT DCS.

Note that preferably $Y_{CT}$ and $Z_{Gantry}$ must be provided for the CT device prior to installation (either from the mechanical drawings or from other sources). Also, $Y_{NM}$ is preferably determined per individual scan by the NM device; $Z_{NMBed}$ and $Y_{NMBed}$ are preferably provided to the NM device by the CT device during the NM scan.

The present invention further assigns image orientation in NM projection images. The "ImageOrientationOnPatient" DICOM attribute (0020, 0037) reflects the image orientation of the first frame of the NM projections with respect to the DICOM PCS. According to the present invention, it is preferable to set the column vector $[cv_x, cv_y, cv_z]$ of any projection image to [0, 0, −1]. The row vector $[rv_x, rv_y, rv_z]$ depends on where the scan starts with respect to the patient and what the viewer's perspective is with respect to the projection image. According to the present invention, it is preferable that each projection is formed such that it lies between the patient and the viewer. For example, if the scan starts from the 45 degree angle between the right and the anterior views, it is [0.707, −0.707, 0].

If no mechanical and installation errors occur, the co-registration scheme of the present invention will perfectly register the acquired CT image and the reconstructed NM volume without any adjustment to the images.

Often, however it is necessary to calibrate the combined CT-NM system to generated a so-called "FOV calibration matrix." This 4×4 matrix preferably records the differences between the two imaging gantries in terms of translation and rotation of the reconstructed volumes. The matrix is then preferably applied to the NM image post reconstruction to align it to the CT image.

Although the present invention has been described in considerable detail with reference to certain preferred versions thereof, other versions are possible. Therefore, the spirit and scope of the appended claims should not be limited to the description of the preferred versions contained herein.

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C §112, sixth paragraph. In particular, the use of "step of" in the claims herein is not intended to invoke the provisions of 35 U.S.C §112, sixth paragraph.

What is claimed is:

1. A method for co-registering a nuclear medical (NM) reconstructed image obtained from an NM scan by an NM scanner having an NM gantry, and a computed tomography (CT) reconstructed image obtained from a CT scan by a CT scanner having a CT gantry in a multimodality imaging system, comprising:

matching a first patient coordinate system of the NM scanner to a second patient coordinate system of the CT scanner, based on a predefined relationship between:
    a vertical position of a patient bed during the NM scan;
    an axial position of the patient bed during the NM scan;
    an axial distance between a gantry of the NM scanner and a gantry of the CT scanner; and
    a vertical distance between a center of orbit of the NM scanner and a center of rotation of the CT gantry;

assigning an X-coordinate ($X_{img}$) to the CT reconstructed image by:
    specifying a row vector $[rv_x, rv_y, rv_z]$ to reflect the orientation of the CT reconstructed image relative to the second patient coordinate system, and
    determining a distance ($X_{center}$) from a center of the second patient coordinate system and a transverse extents of the CT reconstructed image centered at an image center point (FOV).

2. The method according to claim 1, wherein $X_{img}$ is determined according to Equation 1:

$$X_{img} = X_{center} - (rv_x)(½)(FOV_{CT}) \quad (1)$$

where (½) ($FOV_{CT}$) is given by Equation 2:

$$(½)(FOV_{CT}) = (MatrixSize_{CT} - 1)(PixelSize_{CT}/2) \quad (2)$$

where $MatrixSize_{CT}$ is the image area of the CT scanner in pixels, and wherein $PixelSize_{CT}$ is the size of a pixel in a CT image.

3. The method according to claim 1, further comprising assigning an X coordinate ($X_{NMImg}$) to the NM reconstructed image by:

specifying a distance ($X_{NMCenter}$) in an X direction between the center of the NM reconstructed image and a center of the first patient coordinate system as 0, and specifying a row vector $[rv_x, rv_y, rv_x]$ to reflect the orientation of the NM reconstructed image relative to the first patient coordinate system, such that the row vector is [1, 0, 0].

4. The method according to claim 3, wherein $X_{NMImg}$ is determined according to Equation 3:

$$X_{NMImg} = (MatrixSize_{NM} - 1)(PixelSize_{NM}/2) \quad (3)$$

where MatrixSize$_{NM}$ is the image area of the NM scanner in pixels, and wherein PixelSize$_{NM}$ is the size of a pixel in a NM image.

5. The method according to claim 1, further comprising assigning a Z-coordinate ($Z_{img}$) to the CT reconstructed image based on the orientation of a patient on a CT bed, associated with the CT scanner.

6. The method according to claim 1, further comprising assigning a Z coordinate ($Z_{NMImg}$) to the NM reconstructed image by:
   specifying a column vector [cv$_x$, cv$_y$, cv$_z$] as [0, 0, −1],
   specifying $Z_{NMImg}$ as the top row of the column vector.

7. The method according to claim 6, further comprising determining a Z-position for at least one addition row based on the column vector and a distance of the additional row from the top row ($Z_{NMIMg}$).

8. The method according to claim 7, wherein the Z-position of at least one additional row is the Z-position of a center row of the NM reconstructed image ($Z_{NMCenter}$), and wherein $Z_{NMCenter}$ is specified according to Equation 6:

$$Z_{NMCenter}=Z_{NMImg}+(CV_z)(\tfrac{1}{2})(FOV_{NM})=Z_{NMImg}-(\tfrac{1}{2})(FOV_{NM}) \quad (6)$$

where ($\tfrac{1}{2}$) (FOV$_{NM}$) is given by Equation 2:

$$(\tfrac{1}{2})(FOV_{NM})=(MatrixSize_{NM}-1)(PixelSize_{NM}/2) \quad (2)$$

wherein MatrixSize$_{NM}$ is the image area of the NM scanner in pixels, and wherein PixelSize$_{NM}$ is the size of a pixel in a NM image.

9. The method according to claim 1, further comprising assigning a Y-coordinate ($Y_{img}$) to the CT reconstructed image by:
   specifying a column vector [cv$_x$, cv$_y$, cv$_z$] to reflect the orientation of the CT reconstructed image relative to the second patient coordinate system, and
   determining a distance ($Y_{center}$) from a center of the second patient coordinate system and a transverse extents of the CT reconstructed image centered at an image center point (FOV).

10. The method according to claim 8, wherein a patient is scanned in a prone position and the column vector is specified as [0, −1, 0].

11. The method according to claim 8, wherein a patient is scanned in a supine position and the column vector is specified as [0, 1, 0].

12. The method according to claim 1, wherein
   assigning a Y coordinate ($Y_{NMImg}$) to the NM reconstructed image by:
   specifying a distance ($Y_{NMCenter}$) in a Y direction between the center of the NM reconstructed image and a center of the first patient coordinate system as 0, and
   specifying a column vector [cv$_x$, cv$_y$, cv$_z$] to reflect the orientation of the NM reconstructed image relative to the first patient coordinate system, such that the row vector is [0, 1, 0].

13. The method according to claim 12, wherein, for supine scans, $Y_{NMImg}$ is determined according to Equation 14:

$$Y_{NMImg}=Y_{NMCenter}-Y_{NMBed}-(\tfrac{1}{2})(FOV_{NM}) \quad (14).$$

14. The method according to claim 12, wherein, for prone scans, $Y_{NMImg}$ is determined according to Equation 15:

$$Y_{NMImg}=Y_{NMBed}-Y_{NMCenter}-(\tfrac{1}{2})(FOV_{NM}) \quad (15).$$

15. A device for co-registering a nuclear medical (NM) reconstructed image obtained from an NM scan by an NM scanner having an NM gantry, and a computed tomography (CT) reconstructed image obtained from a CT scan by a CT scanner having a CT gantry, wherein the device comprises a programmable element, programmed to
   match a first patient coordinate system of the NM scanner to a second patient coordinate system of the CT scanner, based on a predefined relationship between:
      a vertical position of a patient bed during the NM scan;
      an axial position of the patient bed during the NM scan;
      an axial distance between the NM gantry and the CT gantry; and
      a vertical distance between a center of orbit of the NM scanner and a center of rotation of the CT gantry.
   wherein the programmable element is further programmed to:
      assign an X-coordinate ($X_{img}$) to the CT reconstructed image by:
         specifying a row vector [rv$_x$, rv$_y$, rv$_z$] to reflect the orientation of the CT reconstructed image relative to the second patient coordinate system, and
         determining a distance ($X_{center}$) from a center of the second patient coordinate system and a transverse extents of the CT reconstructed image centered at an image center point (FOV).

16. The device according to claim 15, wherein $X_{img}$ is determined according to Equation 1, $$X_{img}=X_{center}-(rv_x)(\tfrac{1}{2})(FOV_{CT}) \quad 1,$$

where ($\tfrac{1}{2}$) (FOV$_{CT}$) is given by Equation 2, $$(\tfrac{1}{2})(FOV_{CT})=(MatrixSize_{CT}-1)(PixelSize_{CT}/2) \quad 2,$$

where MatrixSize$_{CT}$ is the image area of the CT scanner in pixels, and wherein PixelSize$_{CT}$ is the size of a pixel in a CT image.

17. The device according to claim 15, wherein the programmable element is further programmed to assign an X coordinate ($X_{NMImg}$) to the NM reconstructed image by:
   specifying a distance ($X_{NMCenter}$) in an X direction between the center of the NM reconstructed image and a center of the first patient coordinate system as 0, and
   specifying a row vector [rv$_x$, rv$_y$, rv$_z$] to reflect the orientation of the NM reconstructed image relative to the first patient coordinate system, such that the row vector is [1, 0, 0].

18. The device according to claim 17, wherein the programmable element is further programmed to determine $X_{NMImg}$ according to Equation 3:

$$X_{NMImg}=(MatrixSize_{NM}-1)(PixelSize_{NM}/2) \quad (3)$$

wherein MatrixSize$_{NM}$ is the image area of the NM scanner in pixels, and wherein PixelSize$_{NM}$ is the size of a pixel in a NM image.

19. The device according to claim 15, wherein the programmable element is further programmed to assign a Z-coordinate ($Z_{img}$) to the CT reconstructed image based on the orientation of a patient on a CT bed, associated with the CT scanner.

20. The device according to claim 15, wherein the programmable element is further programmed to assign a Z coordinate ($Z_{NMImg}$) to the NM reconstructed image by:
   specifying a column vector [cv$_x$, cv$_y$, cv$_z$] as [0, 0, −1], and by
   specifying $Z_{NMImg}$ as the top row of the column vector.

21. The device according to claim 20, wherein the programmable element is further programmed to determine a Z-position for at least one addition row based on the column vector and a distance of the additional row from the top row ($Z_{NMIMg}$).

22. The device according to claim 21, wherein the Z-position of at least one additional row is the Z-position of a center row of the NM reconstructed image ($Z_{NMCenter}$), and wherein the programmable element is further programmed to specify $Z_{NMCenter}$ according to Equation 6:

$$Z_{NMCenter} = Z_{NMImg} + (CV_z)(\tfrac{1}{2})(FOV_{NM}) = Z_{NMImg} - (\tfrac{1}{2})(FOV_{NM}) \qquad (6)$$

where ($\tfrac{1}{2}$) ($FOV_{NM}$) is given by Equation 2, $$(\tfrac{1}{2})(FOV_{NM}) = (MatrixSize_{NM} - 1)(PixelSize_{NM}/2) \qquad (2)$$

wherein $MatrixSize_{NM}$ is the image area of the NM scanner in pixels, and wherein $PixelSize_{NM}$ is the size of a pixel in a NM image.

23. The device according to claim 15, wherein the programmable element is further programmed to assign a Y-coordinate ($Y_{img}$) to the CT reconstructed image by:

specifying a column vector [$cv_x$, $cv_y$, $cv_z$] to reflect the orientation of the CT reconstructed image relative to the second patient coordinate system, and to determine a distance ($Y_{center}$) from a center of the second patient coordinate system and a transverse extents of the CT reconstructed image centered at an image center point (FOV).

24. The device according to claim 23, wherein the programmable element is further programmed to specify the column vector as [0, −1, 0] when a patient is scanned in a prone position.

25. The device according to claim 23, wherein the programmable element is further programmed to specify the column vector as [0, 1, 0] when a patient is scanned in a supine position.

26. The device according to claim 15, wherein the programmable element is further programmed to assign a Y coordinate ($Y_{NMImg}$) to the NM reconstructed image by:

specifying a distance ($Y_{NMCenter}$) in a Y direction between the center of the NM reconstructed image and a center of the first patient coordinate system as 0, and specifying a column vector [$cv_x$, $cv_y$, $cv_z$] to reflect the orientation of the NM reconstructed image relative to the first patient coordinate system, such that the row vector is [0, 1, 0].

27. The device according to claim 26, wherein, for supine scans, the programmable element is further programmed to determine $Y_{NMImg}$ according to Equation 14:

$$Y_{NMImg} = Y_{NMCenter} - Y_{NMBed} - (\tfrac{1}{2})(FOV_{NM}) \qquad 14.$$

28. The device according to claim 27, wherein, for prone scans, the programmable element is further programmed to determine $Y_{NMImg}$ according to Equation 15:

$$Y_{NMImg} = Y_{NMBed} - Y_{NMCenter} - (\tfrac{1}{2})(FOV_{NM}) \qquad 15.$$

* * * * *